United States Patent
Madsen et al.

(10) Patent No.: US 12,313,441 B2
(45) Date of Patent: *May 27, 2025

(54) AUTOMATED SPLITTING OF A FLUID INTO UNEVEN VOLUMES

(71) Applicant: Fenwal, Inc., Lake Zurich, IL (US)

(72) Inventors: James Madsen, Chicago, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 670 days.

This patent is subject to a terminal disclaimer.

(21) Appl. No.: 17/585,683

(22) Filed: Jan. 27, 2022

(65) Prior Publication Data

US 2022/0244093 A1    Aug. 4, 2022

Related U.S. Application Data

(60) Provisional application No. 63/143,439, filed on Jan. 29, 2021.

(51) Int. Cl.
*G01G 13/26* (2006.01)
*A61M 1/02* (2006.01)
(Continued)

(52) U.S. Cl.
CPC .......... *G01G 17/06* (2013.01); *A61M 1/0209* (2013.01); *A61M 1/0281* (2013.01); *G01G 13/26* (2013.01);
(Continued)

(58) Field of Classification Search
CPC ......... G01G 13/26; G01G 19/18; G01G 23/16
See application file for complete search history.

(56) References Cited

U.S. PATENT DOCUMENTS

| 3,727,066 A | 4/1973 | Louderback et al. |
| 3,752,995 A | 8/1973 | Liedholz |

(Continued)

FOREIGN PATENT DOCUMENTS

| EP | 0342730 A2 | 11/1989 |
| EP | 0771569 A2 | 5/1997 |

(Continued)

OTHER PUBLICATIONS

U.S. Appl. No. 10/561,784 B2 filed Feb. 18, 2020, Katz et al.
Extended European Search Report, dated Jun. 15, 2022, for application No. EP22153558.6-1113.

*Primary Examiner* — Paul J Gray
(74) *Attorney, Agent, or Firm* — Cook Alex Ltd.

(57) ABSTRACT

A system for splitting a fluid includes a source support configured to support a source container and a satellite support configured to support a satellite container fluidly connected to the source container. A weight scale is associated with each of the supports. The system also includes a clamp system and a controller. The controller determines a plurality of possible distributions of the fluid between the source container and the satellite container based at least in part on the concentration or amount of said constituent and the combined weight measured by each weight scale, then controls the clamp system to selectively allow and prevent fluid flow from the source container to the satellite container so as to distribute the fluid between the source container and the satellite container according to one of the distributions, with at least one of the possible distributions being an uneven distribution of the fluid.

12 Claims, 5 Drawing Sheets

(51) Int. Cl.
  *G01G 17/06* (2006.01)
  *G01G 19/18* (2006.01)
  *G01G 23/16* (2006.01)

(52) U.S. Cl.
  CPC .............. *G01G 19/18* (2013.01); *G01G 23/16* (2013.01); *A61M 2202/0427* (2013.01)

(56) References Cited

U.S. PATENT DOCUMENTS

| | | |
|---|---|---|
| 3,778,171 A | 12/1973 | Chervenka |
| 4,120,449 A | 10/1978 | Brown et al. |
| 4,409,820 A | 10/1983 | Nash |
| 4,468,219 A | 8/1984 | George et al. |
| 4,557,719 A | 12/1985 | Neumann et al. |
| 4,604,086 A | 8/1986 | Benko et al. |
| 4,810,090 A | 3/1989 | Boucher et al. |
| 5,104,526 A | 4/1992 | Brown et al. |
| 5,260,598 A | 11/1993 | Brass et al. |
| 5,298,476 A | 3/1994 | Hotta et al. |
| 5,316,666 A | 5/1994 | Brown et al. |
| 5,316,667 A | 5/1994 | Brown et al. |
| 5,400,261 A | 3/1995 | Reynolds |
| 5,437,598 A | 8/1995 | Antwiler |
| 5,570,697 A | 11/1996 | Walker et al. |
| 5,573,678 A | 11/1996 | Brown et al. |
| 5,592,402 A | 1/1997 | Beebe et al. |
| 5,605,842 A | 2/1997 | Langley et al. |
| 5,611,997 A | 3/1997 | Langley et al. |
| 5,628,915 A | 5/1997 | Brown et al. |
| 5,632,893 A | 5/1997 | Brown et al. |
| 5,639,382 A | 6/1997 | Brown |
| 5,656,163 A | 8/1997 | Brown |
| 5,868,696 A | 2/1999 | Giesler et al. |
| 5,948,271 A | 9/1999 | Wardwell et al. |
| 5,958,250 A | 9/1999 | Brown et al. |
| 5,961,842 A | 10/1999 | Min et al. |
| 5,980,757 A | 11/1999 | Brown et al. |
| 5,980,760 A | 11/1999 | Min et al. |
| 6,063,292 A | 5/2000 | Leung |
| 6,254,784 B1 | 7/2001 | Nayak et al. |
| 6,312,607 B1 | 11/2001 | Brown et al. |
| 6,899,666 B2 | 5/2005 | Brown |
| 7,327,443 B2 | 2/2008 | Scibona et al. |
| 7,355,685 B2 | 4/2008 | Scibona et al. |
| 7,422,693 B2 | 9/2008 | Carter et al. |
| 7,605,388 B2 | 10/2009 | Carter et al. |
| 7,951,059 B2 | 5/2011 | Sweat |
| 9,314,562 B2 | 4/2016 | Foley et al. |
| 9,594,020 B2 | 3/2017 | Koudelka et al. |
| 9,861,736 B2 | 1/2018 | Barry, Jr. et al. |
| 2004/0133086 A1 | 7/2004 | Ciurczak et al. |
| 2004/0151633 A1 | 8/2004 | De Gaulle |
| 2007/0239033 A1 | 10/2007 | Tearney et al. |
| 2008/0014181 A1 | 1/2008 | Ariff et al. |
| 2008/0041772 A1 | 2/2008 | Sweat et al. |
| 2008/0045394 A1 | 2/2008 | Kolenbrander et al. |
| 2009/0073456 A1 | 3/2009 | Wax et al. |
| 2009/0129976 A1 | 5/2009 | Hoshino et al. |
| 2011/0058070 A1 | 3/2011 | Awazu |
| 2011/0143905 A1 | 6/2011 | Kolenbrander et al. |
| 2012/0190945 A1 | 7/2012 | Yamanaka et al. |
| 2014/0008277 A1 | 1/2014 | Foley et al. |
| 2014/0030729 A1 | 1/2014 | Basiji et al. |
| 2014/0045668 A1 | 2/2014 | Case et al. |
| 2018/0072977 A1 | 3/2018 | Binninger |
| 2020/0078406 A1 | 3/2020 | Weiner et al. |

FOREIGN PATENT DOCUMENTS

| | | |
|---|---|---|
| EP | 0779077 A1 | 6/1997 |
| WO | WO 96/40319 A1 | 12/1996 |
| WO | WO 03/000026 A2 | 1/2003 |
| WO | WO 03/026724 A1 | 4/2003 |
| WO | WO 2008/021633 A2 | 2/2008 |
| WO | WO 2008/114164 A1 | 9/2008 |
| WO | WO 2014/039091 A1 | 3/2014 |
| WO | WO 2018/053217 A1 | 3/2018 |

AUTOMATED SPLITTING OF A FLUID INTO UNEVEN VOLUMES

CROSS-REFERENCE TO RELATED APPLICATIONS

This application claims the benefit of and priority of U.S. Provisional Patent Application Ser. No. 63/143,439, filed Jan. 29, 2021, the contents of which are incorporated by reference herein.

BACKGROUND

Field of the Disclosure

The present disclosure relates to automated splitting of a fluid. More particularly, the present disclosure relates to apparatus and methods for splitting a high volume fluid into two or more uneven volumes.

Description of Related Art

It is well known to separate blood into its constituents, including separating and collecting a platelet product. A single apheresis platelet donation unit contains approximately $3.0 \times 10^{11}$ platelets suspended in a volume of approximately 200-400 ml of plasma, though a single apheresis procedure may produce a platelet product having a much greater volume, such as approximately $9.6 \times 10^{11}$ platelets suspended in a volume of approximately 700 ml of plasma. In such a scenario, it is typical to split the high volume platelet product into separate amounts each having a volume within the range of what is acceptable for a single unit, with a high volume platelet product typically being split into either two or three units having approximately the same volumes.

The high volume platelet product is conventionally split into individual units according to a manual approach. For example, a platelet product is collected in a collection container of a fluid flow circuit also having at least one secondary container. The fluid flow circuit is weighed to determine the tare weight of the empty containers and the weight of the platelet product. The weight of each container at the end of the procedure (i.e., when a unit of platelets is contained in each) is then calculated by hand. An amount of the high volume platelet product is then flowed out of the collection container and into the secondary container(s) by hand until the volume of platelet product contained by each appears to the technician to be approximately equal. The containers are then weighed to determine whether the volume of each is within the range of what is acceptable for a single unit. If not, the technician repeatedly flows fluid from one container to another until determining that each container contains an appropriate volume of the platelet product. At that time, the containers are typically sealed and separated from each other for storage or use of each as a single unit of platelets.

Before a platelet product may be distributed to a patient, it must first be tested for bacterial contamination or undergo pathogen reduction, as platelet bacterial contamination is a leading risk of infection for patients following transfusion. There are 1- and 2-step versions of bacterial contamination testing, with a blood processing center selecting the best test method based on collected platelet volumes, concentrations, and desired shelf life. Differing volumes and platelet concentrations are required for platelet units undergoing bacterial contamination testing and pathogen inactivation. Thus, according to a conventional, manual approach, a technician attempts to split an amount of platelets into the minimum volume and concentration requirements required for bacterial testing or pathogen reduction by hand using a weight scale. This manual approach lends itself to errors in splitting the product into the proper volumes, while also possibly involving the risk of the technician improperly determining the most efficient distribution for testing or pathogen reduction.

PCT Patent Application No. PCT/US20/42235 (which is hereby incorporated herein by reference) describes a system that improves upon the manual approach by automating the fluid-splitting process.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system for splitting a fluid includes a source support configured to support a source container of a fluid flow circuit, a satellite support configured to support a satellite container of the fluid flow circuit fluidly connected to the source container, a weight scale associated with each of the supports, a clamp assembly, and a controller. The controller is configured to receive an input corresponding to a concentration or an amount of a constituent in a fluid to be split, control each weight scale to measure a combined weight of the container and the contents of the container supported by the support associated with the weight scale, and determine a plurality of possible distributions of the fluid to be split between the source container and the satellite container based at least in part on the concentration or amount of said constituent and the combined weight measured by each weight scale. The controller then controls the clamp system to selectively allow and prevent fluid flow from the source container to the satellite container so as to distribute the fluid to be split between the source container and the satellite container according to one of said plurality of possible distributions, with at least one of said plurality of possible distributions being an uneven distribution of the fluid to be split.

In another aspect, a method is provided for automatically splitting a fluid. The method includes receiving an input corresponding to a concentration or an amount of a constituent in a fluid in a source container to be split between the source container and a satellite container. A combined weight is measured for each container and the contents of the container. A plurality of possible distributions of the fluid to be split between the source container and the satellite container is determined, based at least in part on the concentration or amount of said constituent and the combined weights. A clamp system is then automatically controlled to selectively allow and prevent fluid flow from the source container to the satellite container so as to distribute the fluid to be split between the source container and the satellite container according to one of said plurality of possible distributions, with at least one of said plurality of possible distributions being an uneven distribution of the fluid to be split.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
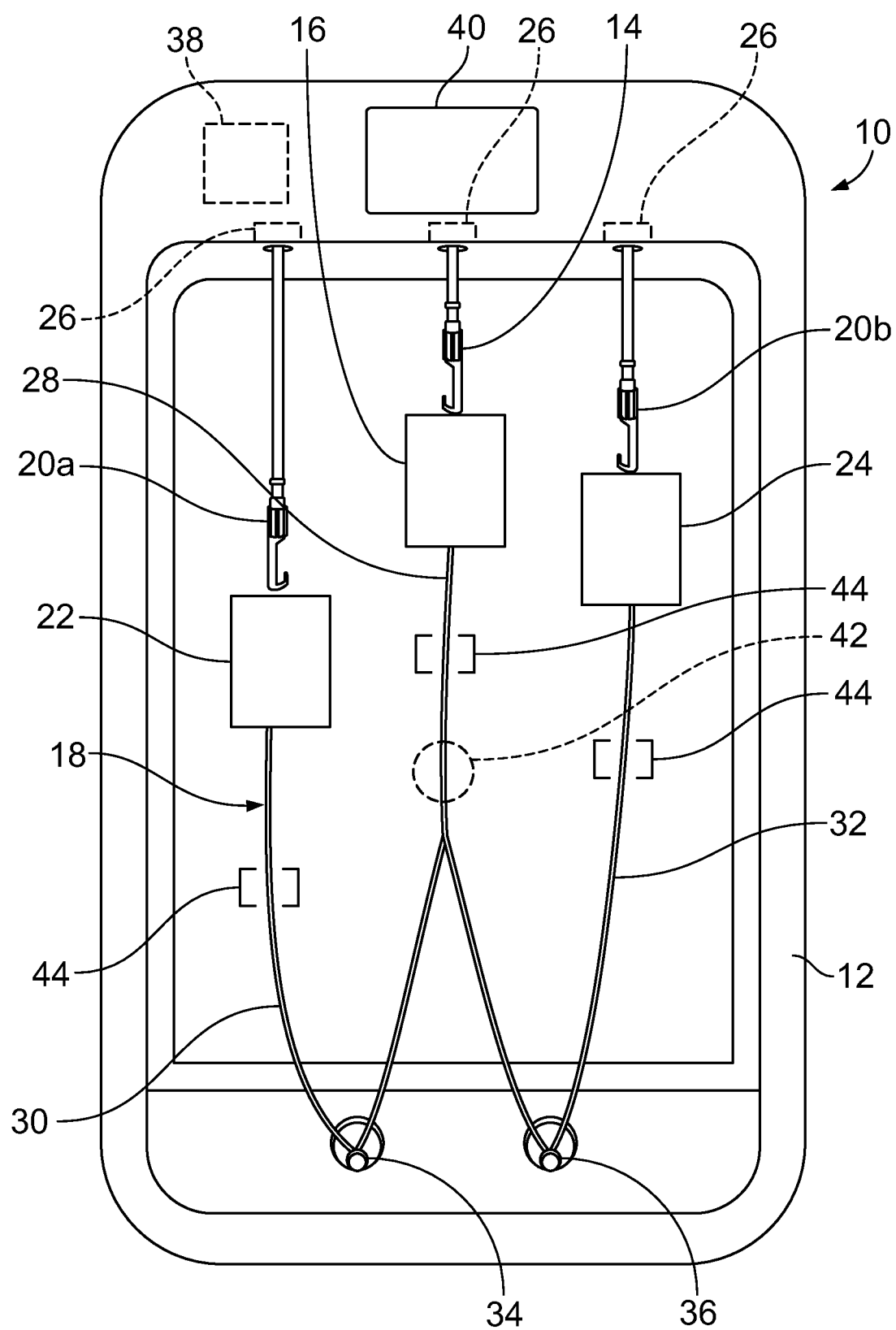
FIG. 1 is a front elevational view of an exemplary embodiment of a system for splitting a fluid into two or more uneven volumes, according to an aspect of the present disclosure.

FIG. 1 depicts an exemplary system 10 for splitting a fluid into two or more uneven volumes. A system 10 of the type shown in FIG. 1 may be particularly advantageous for splitting a high volume platelet product into two or more uneven volumes, but it should be understood that the system 10 is not limited to use with any particular fluid.

The illustrated system 10 includes a frame 12 (at least partially formed of a metallic or rigid material in one embodiment) having a source support 14 configured to support a source container 16 of a fluid flow circuit 18 (which may also be referred to as a source bag or mother container or mother bag). The system 10 is configured as a durable, reusable device, while the fluid flow circuit 18 is typically disposable and configured as a single-use item. However, it is within the scope of the present disclosure for the fluid flow circuit 18 to be configured as a reusable item.

The particular configuration of the source support 14 may vary without departing from the scope of the present disclosure, and may depend upon the nature of the source container 16 that it is intended to support (with the configuration of the source container 16 also being subject to variation without departing from the scope of the present disclosure). For example, in one embodiment, the source container 16 is configured as a flexible bag having an upper opening or aperture. In this case, the source support 14 may include or be configured as a hook or hanger, which includes a portion that extends into and through the upper opening or aperture of the source container 16 to support and suspend the source container 16 at some elevation. In other embodiments, the source support 14 may be differently configured, such as being configured as a horizontal surface onto which the source container 16 may be placed.

The frame 12 further includes first and second satellite supports 20a and 20b, which are each configured to support a different satellite container 22, 24 of the fluid flow circuit 18. The satellite supports 20a and 20b may be similarly configured to the source support 14 or may be differently configured. Similarly, the satellite containers 22 and 24 may be similarly configured to the source container 16 or may be differently configured. While FIG. 1 illustrates a fluid flow circuit 18 having a pair of satellite containers 22 and 24, it should be understood that the system 10 may also be used in combination with a fluid flow circuit having only one satellite container. Additionally, it should be understood that systems according to the present disclosure are not limited to any particular number of satellite supports (and satellite containers) and that it is within the scope of the present disclosure for a high volume fluid to be split into any number of volumes.

Each support 14, 20a, 20b of the illustrated system 10 has a weight scale 26 associated with it. In the illustrated embodiment, the weight scales 26 are shown as being separate from each other, but it should be understood that they may be associated in some manner as parts of a weighting system or assembly. The weight scales 26 may be similarly or differently configured. Regardless of the particular configuration, each weight scale 26 is configured to measure a combined weight of the container that it is supporting (i.e., the tare weight) and the contents of that container. By knowing the weight of the empty container and the combined weight, the weight of any fluid in the container may be calculated by subtracting the tare weight from the combined weight.

While each support is described and illustrated as including an associated weight scale, it is contemplated that one support of a given frame could be provided without an associated weight scale or that one of the weight scales could be inactive during a fluid-splitting procedure. In one example, if the volume of the source container is known to be the same from procedure to procedure or is input by an operator, then the source support could omit a weight scale (or have an inactive weight scale) because the volume to be distributed could be calculated. In another example, if the tare weights of the satellite containers were known to be identical from procedure to procedure, then one of the satellite supports could omit a weight scale (or have an inactive weight scale).

In addition to the containers 16, 22, and 24, the fluid flow circuit 18 further includes a plurality of conduits connecting the various containers. In the illustrated embodiment, the source container 16 includes an associated main conduit 28, with first and second branch conduits 30 and 32 fluidly connected to and extending from the main conduit 28 to the first and second satellite containers 22 and 24 (respectively). While FIG. 1 shows the conduits 30 and 32 leading to the satellite containers 22 and 24 branching off from a single or common conduit 28 connected to the source container 16, in other embodiments, each branch conduit 30 and 32 may instead extend directly between the associated satellite container 22, 24 and the source container 16.

Regardless of the exact configuration of the fluid flow circuit 18, the system 10 includes a clamp assembly configured to selectively allow and prevent fluid flow through the conduits of the fluid flow circuit 18. In the illustrated embodiment, each branch conduit 30, 32 is placed into association with a corresponding clamp or valve 34, 36 of the clamp assembly when the fluid flow circuit 18 is mounted to the frame 10. Although not illustrated in FIG. 1, it is also within the scope of the present disclosure for the clamp assembly to include an additional clamp or valve that may regulate flow through the main conduit 28. In one embodiment, the individual clamps 34 and 36 of the clamp assembly are configured to be automatically (i.e., non-manually) moved between closed and open conditions. In the open condition, the clamp or valve allows fluid flow through the associated conduit. In the closed condition, the clamp or valve prevents fluid flow through the associated conduit. The manner in which the clamp or valve prevents fluid flow through the associated conduit may vary depending on the configurations of the clamp or valve and the conduit. For example, in one embodiment, each branch conduit 30, 32 is configured as a flexible tube, with the corresponding clamp or valve configured as a pinch valve, which may squeeze the conduit to close it, thereby preventing fluid flow through the conduit. If a conduit is differently configured (e.g., as a rigid tube), the clamp assembly may be differently configured (e.g., as a ball valve) to selectively allow and prevent fluid flow through the conduit.

The weight scales 26 and the clamp assembly communicate with a controller 38. The controller 38 carries out process control and monitoring functions for the system 10. The controller 38 comprises a main processing unit (MPU), which can comprise, e.g., a Pentium™ type microprocessor made by Intel Corporation, although other types of conventional microprocessors can be used. In the illustrated embodiment, the controller 38 is incorporated into the frame 12, but it should be understood that the controller 38 may be incorporated into a separate component of the system 10, such as a computer that is associated with the weight scales 26 and the clamp assembly by a wired or wireless connection.

The controller 38 receives data or signals from the weight scales 26 to determine the weight of the fluid in each container 16, 22, 24 throughout the course of a fluid-splitting procedure, as the weight of the fluid in each container will change during a procedure due to fluid being conveyed from one of the containers to another (as will be described in greater detail). Based on the weight of the fluid in each container 16, 22, 24, the controller 38 controls the clamp assembly to allow or prevent fluid flow through the various conduits at any particular time, as appropriate to place the targeted volumes of fluid in each container 16, 22, 24 at the end of the procedure.

In the illustrated embodiment, the controller 38 is mounted inside the frame 12, adjacent to or incorporated into an operator interface station 40. The operator interface station 40 (which is shown in greater detail in FIG. 2) displays various information regarding a fluid-splitting procedure and/or allows an operator to provide information and instructions to the controller 38, as will be described in greater detail herein. In one embodiment, the operator interface station 40 is configured as or includes a touchscreen, which allows an operator to provide information and instructions to the controller 38 by pressing icons displayed on a screen. In another embodiment, the operator interface station includes separate devices for providing information and instructions to the controller 38 (which device may be configured as a computer or a smartphone or tablet, for example) and for displaying information regarding a fluid-splitting procedure (e.g., a display screen incorporated into the frame 12).

In an exemplary procedure using the system 10 of FIG. 1, the fluid flow circuit 18 is mounted to the frame 12, with the source container 16 supported by the source support 14 and the satellite containers 22 and 24 supported by the satellite supports 20a and 20b. The containers 16, 22, and 24 may be initially empty to allow for the weight scales 26 and the controller 38 to determine the tare weight of each. Alternatively, the tare weights of the containers 16, 22, and 24 may be otherwise determined (e.g., by weighing them using a separate weighting system), with the tare weights being provided to the controller 38.

Regardless of how the tare weights of the containers 16, 22, and 24 are determined, once they are known to the controller 38, the fluid flow circuit 18 is mounted to the frame 12, with the source container 16 supported by the source support 14 and at least partially filled with a fluid, the first satellite container 22 supported by one of the satellite supports 20a, the second satellite container 24 supported by the other satellite support 20b, and a portions of the branch conduits 30 and 32 received by the clamp assembly. It is within the scope of the present disclosure for an amount of fluid to be initially contained in one or both of the satellite containers 22 and 24, though it is more typical for only the source container 16 to contain an amount of fluid, with the satellite containers 22 and 24 being empty.

With the fluid-containing fluid flow circuit 18 mounted to the frame 12, the controller 38 may begin a fluid-splitting procedure in which fluid is transferred from the source container 16 to the other containers 22 and 24 until targeted volumes of fluid are contained in each. The manner in which fluid is conveyed from the source container 16 to the satellite containers 22 and 24 may vary without departing from the scope of the present disclosure. In the illustrated embodiment, the source support 14 is positioned at a greater elevation than the satellite supports 20a and 20b, which allows for fluid flow from the source container 16 to the satellite containers 22 and 24 via gravity. According to a gravity-based approach, the clamp assembly is opened by the controller 38 to allow fluid to flow from the source container 16 to one or both of the satellite containers 22 and 24 under the force of gravity while the controller 38 monitors the weights reported by the weight scales 26. Once the controller 38 determines that the proper volumes of fluid are in each container, the controller actuates the clamp assembly to prevent further flow from the source container 16 to the satellite containers 22 and 24 via the respective branch conduits 30 and 32.

In the illustrated embodiment, each satellite support 20a, 20b is positioned at a different elevation, with each being positioned at a lower elevation than the source support 14. By such a configuration, fluid may be conveyed from the source container 16 to the satellite containers 22 and 24 via gravity, with the higher satellite container 24 filling more quickly than the lower satellite container 22 (assuming that fluid is allowed to freely flow from the source container 16 into the satellite containers 22 and 24). Upon the controller 38 receiving a signal from the weight scale 26 indicating that the upper satellite container 24 has been filled to the desired level, the controller 38 may actuate the clamp assembly to prevent further fluid flow through the branch conduit 32 connected to the upper satellite container 24. Fluid flow from the source container 16 to the lower satellite container 22 continues until the controller 38 receives a signal from the weight scale 26 indicating that the lower satellite container 22 has been filled to the desired level, at which time the controller 38 may actuate the clamp assembly to prevent further flow out of the source container 16.

Filling one satellite container before the other satellite container may be advantageous to the extent that it allows for the controller 38 to execute an initial check of the amount of fluid in the first-filled satellite container before fluid flow out of the source container 16 is completed. If the controller 38 determines that an additional amount of fluid should be conveyed into the first-filled satellite container, then the controller 38 may actuate the clamp assembly to allow for further flow into the first-filled satellite container.

In another embodiment, rather than the satellite supports 20a and 20b being positioned at different elevations, two or more satellite supports may be positioned at the same elevation, which may be lower than the elevation at which the source support is positioned. In such an embodiment, fluid would tend to flow (under the force of gravity) from the source container into the satellite containers at approximately the same rate. If the satellite containers are to be filled to the same level, this would result in the satellite containers being filled to completion at approximately the same time, assuming that fluid flow from the source container 16 to each satellite container 22, 24 begins at the same time.

It should be understood that fluid flow from the source container 16 to the satellite containers 22 and 24 may be initiated simultaneously or sequentially. Additionally, the controller 38 may be configured to allow for simultaneous flow into the satellite containers 22 and 24 or may control the clamp assembly to allow for flow from the source container 16 into only one satellite container at a time. This may include flowing fluid from the source container 16 into one of the satellite containers until that satellite container is filled to the desired level before any fluid is conveyed from the source container 16 into the other satellite container or may instead involve fluid being alternately conveyed into one satellite container and then the other, with the destination of fluid flow being changed multiple times before either satellite container is filled to the desired level. Filling one satellite container to the target level before begin flow into the other satellite container may be advantageous in terms of accuracy (as small adjustments could be made to the amount of fluid in the first satellite container to be filled before allowing flow into the other satellite container), but may take longer than other approaches.

In one embodiment, fluid is allowed to flow into both satellite containers 22 and 24 at the same time, with flow into one of the satellite containers being closed at some point before its weight has reached the target level. In the case of gravity-based flow using the system 10 of FIG. 1 to fill the satellite containers 22 and 24 to the same volume (with the source container containing a different volume of fluid at the end of the procedure), the upper satellite container 24 would tend to fill more quickly than the lower satellite container 22, such that the controller 38 would act to prevent the upper satellite container 24 from being filled to its target level. The other satellite container (which may be the lower satellite container 22 in a gravity-based approach) is filled to the desired volume and then the controller 38 actuates the clamp assembly to prevent further fluid flow into that satellite container. The controller 38 then actuates the clamp assembly to again allow flow into the first satellite container (which may be the upper satellite container 24). So actuating the clamp assembly toward the end of the procedure allows for a system check and small adjustments if fluid volumes do not match the desired volume split.

Opening flow to all satellite containers at the same time and ending flow into them at the same time has the possible advantage of completing a procedure more quickly than other flow patterns. However, such an approach may sacrifice the ability to execute a mid-procedure volume check and/or small volume adjustments at the end of a procedure. If the system 10 operates sufficiently precisely that such checks and adjustments are not required, then it may be advantageous for fluid flow into all satellite containers to begin and end at the same time (if appropriate in view of the desired fluid distribution) in order to reduce processing time.

In another embodiment, rather than relying upon gravity to convey fluid through the fluid flow circuit 18, the system 10 may include a pump system 42 configured to convey fluid from one container to another container. The pump system 42 (if provided) may be variously configured without departing from the scope of the present disclosure. In an exemplary embodiment in which the conduits are configured as flexible tubes, the pump system 42 may include a peristaltic pump, for example, to convey fluid through the main conduit 28.

If a pump system 42 is provided, the relative elevations of the supports 14, 20a, and 20b are less important than in embodiments relying solely upon gravity for fluid transfer. Additionally, if a pump system 42 is provided, the controller 38 may be configured to allow for transfer fluid through the conduits in either direction, which may not be possible in a gravity-based system (except those embodiments in which the relative elevations of the source support 14 and the satellite supports 20a and 20b may be changed). This may be advantageous if the controller 38 determines that too much fluid has been transferred from one container to another container, in which case the controller 38 may control the pump system 42 to convey fluid through the conduit in the opposite direction to bring the fluid levels in the containers to the proper levels. Pumping fluid between the containers may also allow for quicker completion of a procedure compared to what is possible using a gravity-based approach.

Another opportunity created by a pump system 42 is the ability for the controller 38 to be configured to control operation of the clamp assembly based at least in part on the operation of the pump system 42. For example, at the beginning of a procedure, the controller 38 will know the amounts of fluid initially in each container and the amounts of fluid to be contained in each container at the end of the procedure. During the course of the procedure, the controller 38 will also know (and control) the rate of operation of the pump system 42. Based on the volumetric flow rate of the pump system 42 during the course of the procedure, the controller 38 may determine the amount of fluid that has been conveyed from one container to other containers, along with the level of fluid in each container. When the controller 38 has determined that the proper volumes of fluid are present in each container (based at least in part upon the volumetric flow rate of the pump system 42), the controller 38 stops operation of the pump system 42 and actuates the clamp assembly to prevent further flow between the containers.

While use of a pump system 42 may have several advantages, it may also increase the size and cost of the frame 12. Additionally, a pump system 42 may also require use of a particular fluid flow circuit, whereas a gravity-based approach may be used with a wide range of fluid flow circuits. Different collection centers have different priorities and needs, with some that would prefer the flexibility and lower cost of a gravity-based system and other preferring the added functionality of a pump-based system. It should be understood that, even if a frame 12 is provided with a pump system 42, it is within the scope of the present disclosure for the pump system 42 to remain inactive and for fluid to be transferred from one container to another via gravity.

Regardless of how fluid is conveyed from one container to the others, once the proper volumes of fluid are in each container, the controller 38 may actuate a sealing system 44 (if provided). The sealing system 44 seals at least one conduit in at least one location to prevent fluid flow therethrough, thereby ensuring that the proper volumes of fluid remain in each container at the end of a procedure. In the illustrated embodiment, the sealing system 44 is configured to seal the conduits at three locations, one of which is directly adjacent to the source container 16, with the other two being directly adjacent to the satellite containers 22 and 4. The configuration of the sealing system 44 may vary without departing from the scope of the present disclosure. In an exemplary embodiment in which the conduits are configured as flexible tubes, the sealing system 44 may be configured to seal the conduits via a heat seal, with a conduit being pressed shut and then heat being applied (by a radio frequency generator, for example) to melt the walls of the conduit together.

The sealing system 44 may be further configured to sever the conduits at the locations of the seals to allow for separate transport, storage, and/or use of the containers 16, 22, and 24. A seal may be severed by a blade or the like or by any suitable approach, which may vary depending on the natures of the conduits and the seal.

Turning now to particular approaches to splitting a high volume fluid, as explained above, there are also circumstances in which it is preferred to split a fluid into uneven volumes. For example, when the fluid to be split is a platelet product, it may be advantageous to split the fluid into a first volume for bacterial testing and into a second volume for pathogen reduction. Bacterial testing may require a 200 ml volume of fluid, whereas pathogen reduction may require a 255 ml volume of fluid, such that splitting the fluid into a first volume for bacterial testing and a second volume for pathogen reduction would require an uneven split. Such an uneven split may be advantageous for any of a number of reasons, which may include the intended uses of the platelet product (e.g., if a center has a preference for distributing the platelet product into one bacterial testing volume and one pathogen reduction volume, rather than two pathogen reduction volumes) or an attempt to minimize a remainder volume or amount of fluid that is not specifically designated for a target volume (e.g., 710 ml of fluid split into a 200 ml bacterial testing volume and two 255 ml pathogen reduction volumes will have a remainder volume of 0 ml, whereas splitting the fluid into two 200 ml bacterial testing volumes and a 255 pathogen reduction volume would have a remainder volume of 55 ml).

Figure 2:
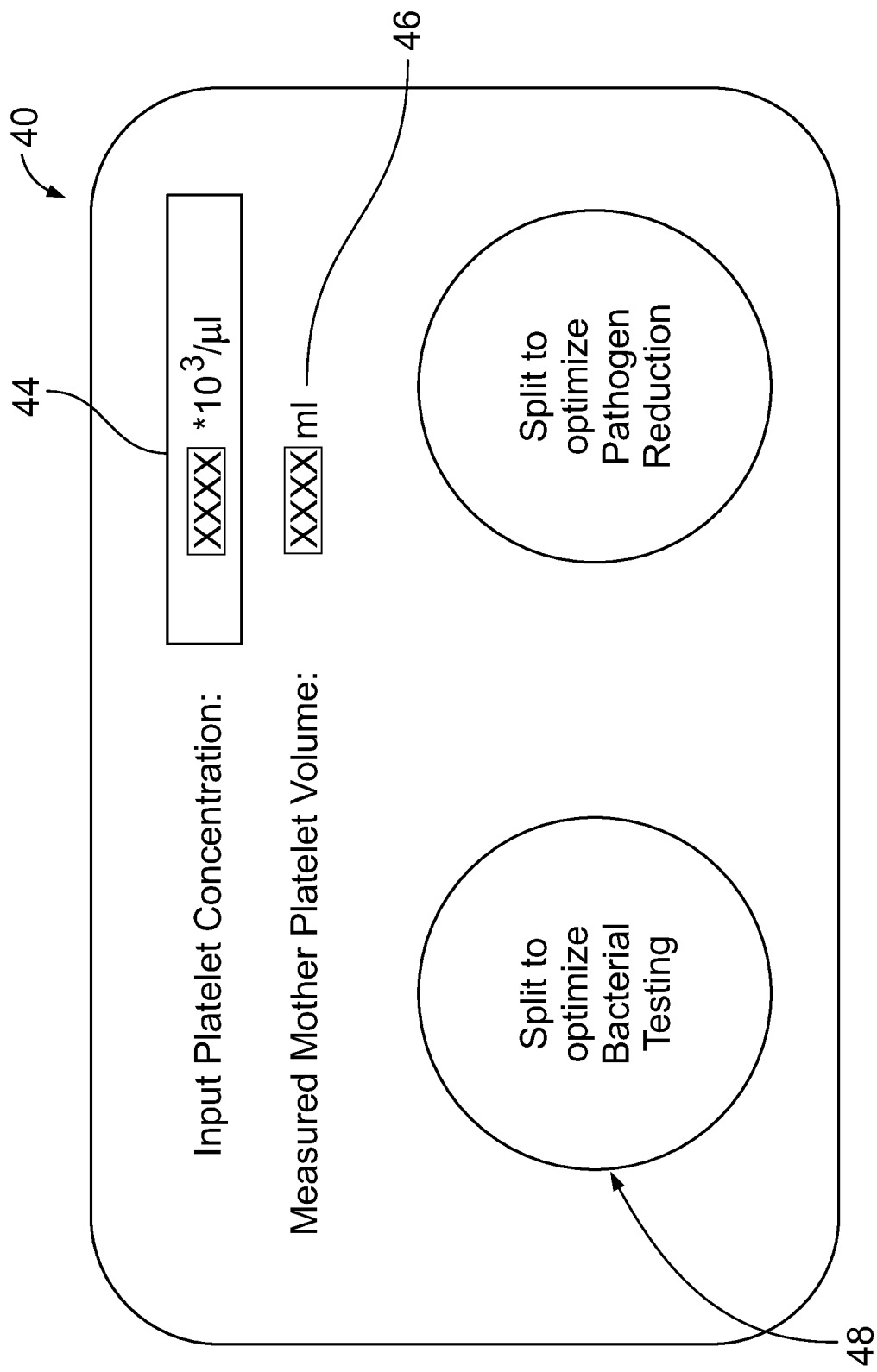
FIG. 2 is a detail view of a operator interface station of the system of FIG. 1.

According to one aspect of the present disclosure, the controller 38 is provided with the concentration or amount of a constituent (e.g., platelets) of a fluid to be split (e.g., a high volume platelet product). FIG. 2 shows an embodiment in which the operator interface station 40 includes a first region 44 displaying the concentration of the constituent, which may be provided by an operator or by some other source (e.g., a network server or database), with a second region 46 displaying the volume of fluid in the fluid flow circuit 18 (which is typically entirely contained within the source container or mother bag 16), as determined by the weight scales 26. Using the concentration or amount of the constituent and the total fluid volume, the controller 38 may determine a plurality of possible distributions of the high volume fluid, with at least one of the distributions that is considered by the controller 38 being an uneven distribution of the fluid (e.g., into one bacterial testing volume and one pathogen reduction volume, in the case of a high volume platelet product to be split).

Once the controller 38 has determined which of the distributions are practicable (as certain distributions may be impossible due to fluid volume and/or the amount or concentration of the constituent), the controller 38 may take any of a number of possible actions. In the embodiment shown in FIG. 2, the controller 38 instructs the operator interface station 40 to display (in a third region 48) two or more distributions into which the high volume fluid may be split. In the illustrated embodiment, the operator interface station 40 displays a first distribution in which a high volume platelet product is distributed in order to optimize bacterial testing and a second distribution in which pathogen reduction is optimized. The operator may select one of the displayed distributions, followed by the controller 38 controlling the other components of the system 10 (most notably, the clamp system) to execute a fluid-splitting procedure that results in the selected distribution. In a variation of this approach, rather than restricting the operator to selecting between the displayed options, the controller 38 may be configured to allow an operator to select a distribution that is different from the displayed options.

In another embodiment, rather than relying upon operator input, the controller 38 may instead be configured to automatically proceed with a fluid-splitting procedure after assessing the possible distributions. If more than one distribution is practicable, the controller 38 may select one based on a preprogrammed or predetermined hierarchy (e.g., selecting the distribution that minimizes the residual volume or distributes the fluid in the way that most closely aligns with the goals of the center).

As described above, in the specific case of a high volume platelet product to be split, two possible distributions of the fluid result in optimization for bacterial testing and for pathogen reduction. As also described above, a bacterial testing volume will be different from a pathogen reduction volume, with a bacterial testing volume being 200 ml (for example) and a pathogen reduction volume being 255 ml (for example). It should be understood that optimization of bacterial testing and/or pathogen reduction is not limited to these two target volumes, but that other volumes are also possible. For example, a 255-325 ml volume of fluid (with a platelet count in the range of $2.9\text{-}5.0 \times 10^{11}$) may be considered a "small volume" pathogen reduction volume, with a 325-390 ml volume (with a platelet count in the range of $3.0\text{-}6.0 \times 10^{11}$) being considered a "large volume" pathogen reduction volume and a 375-420 ml volume (with a platelet count in the range of $6.1\text{-}8.0 \times 10^{11}$) being considered a "dual storage" pathogen reduction volume (which may be pathogen-reduced and then split into two smaller volumes for separate use). Thus, the controller 38 may consider these various volumes when determining how to possibly or optimally split the high volume platelet product, which may include splitting the fluid into two pathogen reduction volumes having different volumes (e.g., splitting a 630 ml volume into a 255 ml "small volume" amount and a 375 ml "large volume" amount).

Figure 3:
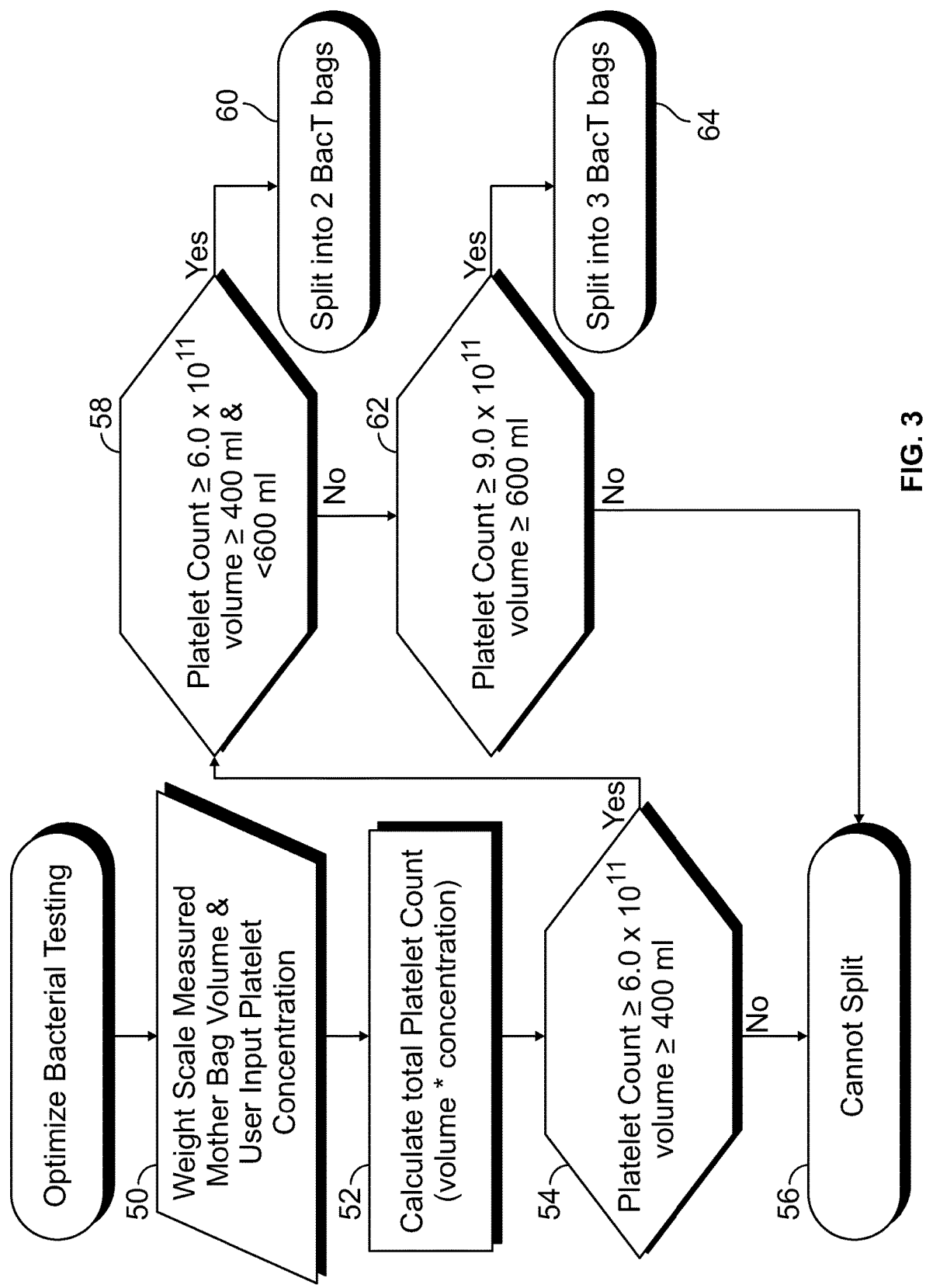
FIG. 3 is a flowchart of an exemplary approach to splitting a fluid into uneven volumes, according to an aspect of the present disclosure.

FIG. 3 shows an exemplary algorithm that may be executed by the controller 38 in order to determine a distribution for optimizing bacterial testing. In a first step (indicated at 50), the weight scales 26 determine the total weight of the fluid flow circuit 18 (which may be used to determine the volume of the fluid to be split), with the controller 38 receiving the platelet concentration of the fluid as an input. The controller 38 then determines the relevant characteristics of the fluid. In the embodiment of FIG. 3, the relevant characteristics of the fluid are the platelet count and the volume of the fluid, but the relevant characteristics of the fluid may be different without departing from the scope of the present disclosure. In the illustrated embodiment, the controller 38 uses the platelet concentration and the volume of the fluid to determine the amount of platelets in the fluid (by multiplying the volume of the fluid by the platelet concentration), as shown in FIG. 3 as step 52. As described above, rather than receiving a constituent concentration as an input, the controller 38 may instead receive a platelet count as an input during step 50, in which case step 52 may be omitted (or instead modified to calculate platelet concentration, if necessary).

Once the relevant characteristics of the fluid have been determined, the controller 38 then determines whether the fluid is suitable for being split so as to optimize bacterial testing. This determination may be made in any of a number of ways, with FIG. 3 showing a step 54 in which the controller 38 compares the platelet count and the volume of the fluid (which are the relevant characteristics in the illustrated embodiment) to be split to minimum values to determine whether it is possible to split the high volume platelet product so as to optimize bacterial testing. In the illustrated embodiment, the minimum platelet count for splitting is $6.0 \times 10^{11}$, while the minimum fluid volume is 400 ml, such that the controller 38 will determine (at step 56) that bacterial testing optimization is not a viable option or distribution. It should be understood that these minimum values are merely exemplary and that other minimum values may be employed without departing from the scope of the present disclosure. For example, different minimum values may be appropriate if the possible target volumes into which a high volume platelet product may be split are different from the ones described herein.

When the controller 38 determines that the high volume fluid is suitable to be distributed so as to optimize bacterial testing, it considers the most appropriate distribution of the fluid based on the relevant characteristics of the fluid and the number of containers that are incorporated into the fluid flow circuit 18 mounted to the frame 12 (because the number of containers determines the maximum number of volumes into which the fluid may be split). In the illustrated embodiment, the fluid flow circuit 18 includes three containers 16, 22, and 24, such that the fluid may be split into either two or three bacterial testing volumes.

The controller 38 first determines whether the fluid is suitable to be split into two bacterial testing volumes. In the embodiment of FIG. 3 (in which a bacterial testing volume has a volume of 200 ml), the controller 38 determines in step 58 whether the fluid contains at least $6.0 \times 10^{11}$ platelets and a volume between 400-600 ml. If so, the controller 38 determines (at step 60) that it is most optimal to split the fluid into two bacterial testing volumes. Depending on the exact volume of the fluid, the two bacterial testing volumes may have the same or different volumes. For example, if the high volume platelet product has a volume of 400 ml, it will be distributed so as to create two bacterial testing volumes each having a volume of 200 ml. This may include all of the fluid being conveyed from the source container 16 into the two satellite containers 22 and 24 or (perhaps more preferably) 200 ml of fluid being transferred from the source container 16 to one of the satellite containers 22, 24. The latter approach may be preferred on account of it being completed more quickly than the former approach (as only half as much fluid is conveyed out of the source container 16), but both approaches are within the scope of the present disclosure.

On the other hand, if the high volume platelet product has a volume greater than 400 ml, the controller 38 may distribute the fluid into equal or unequal volumes. As when splitting the fluid into two equal amounts, the controller 38 may either distribute the fluid between the two satellite containers 22 and 24 (if the fluid flow circuit 18 is provided with at least two satellite containers) or may convey a selected amount into one satellite container 22, 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to one of the satellite containers 22, 24, while retaining the remaining fluid in the source container 16. Thus, if the high volume platelet product has a volume of 500 ml, the controller 38 may execute a fluid-splitting procedure in which 200 ml of fluid are conveyed into one of the satellite containers 22, 24, with the remaining 300 ml remaining in the source container 16. In another embodiment, if a satellite container 22, 24 has a maximum capacity, the controller 38 may be configured to fill the satellite container 22, 24 to its capacity (or to a particular percentage of its capacity), with the remainder of the fluid being retained in the source container 16.

If the controller 38 determines in step 58 that bacterial testing is not optimized by distributing the fluid into two bacterial testing volumes (e.g., due to there being more than 600 ml of fluid to distribute in the embodiment of FIG. 3), the controller 38 determines whether the fluid is suitable to be split into three bacterial testing volumes. In the embodiment of FIG. 3 (in which a bacterial testing volume has a volume of 200 ml), the controller 38 determines in step 62 whether the fluid contains at least $9.0 \times 10^{11}$ platelets and a volume greater than 600 ml. If so, the controller 38 determines (at step 64) that it is most optimal to split the fluid into three bacterial testing volumes. Depending on the exact volume of the fluid, the three bacterial testing volumes may have the same or different volumes. For example, if the high volume platelet product has a volume of 600 ml, it will be distributed so as to create three bacterial testing volumes each having a volume of 200 ml. If the fluid flow circuit 18 includes only two satellite containers 22 and 24, portions of the fluid are transferred to the satellite containers 22 and 24, while the remainder is retained in the source container 16. However, if the fluid flow circuit includes at least three satellite containers, all of the fluid may instead be transferred from the source container to the satellite containers. As explained above, it may be preferred for a bacterial testing volume to remain in the source container 16 due to such a fluid-splitting procedure being completed more quickly (on account of less fluid being conveyed out of the source container 16), though both approaches are within the scope of the present disclosure.

On the other hand, if the high volume platelet product has a volume greater than 600 ml, the controller 38 may distribute the fluid into equal or unequal volumes. As when splitting the fluid into three equal amounts, the controller 38 may either distribute the fluid between three satellite containers (if available) or may convey a selected amount into two satellite containers 22 and 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to the two satellite containers 22 and 24, while retaining the remaining fluid in the source container 16. Thus, if the high volume platelet product has a volume of 700 ml, the controller 38 may execute a fluid-splitting procedure in which 200 ml of fluid are conveyed into each of the satellite containers 22 and 24, with the remaining 300 ml remaining in the source container 16. In another embodiment, if the satellite containers 22 and 24 have a maximum capacity, the controller 38 may be configured to fill the satellite containers 22 and 24 to their capacity (or to a particular percentage of their capacity), with the remainder of the fluid being retained in the source container 16.

If the controller 38 determines in step 62 that bacterial testing is not optimized by distributing the fluid into three bacterial testing volumes (e.g., due to there being fewer than $9.0\times10^{11}$ platelets in the embodiment of FIG. 3), the controller 38 determines that the fluid cannot be distributed so as to optimize bacterial testing (at step 56). On the other hand, if the controller 38 has determined that bacterial testing may be optimized (by splitting the fluid into two or three bacterial testing volumes in the embodiment of FIG. 3), it may present an operator (e.g., in region 48 of the operator interface station 40) with optimization of bacterial testing as a possible distribution or, alternatively, proceed to automatically distribute the fluid so as to optimize bacterial testing (if the controller 38 has been programmed with optimization of bacterial testing as a top priority or preference).

In the illustrated embodiment, the controller 38 also determines whether the high volume platelet product may be distributed so as to optimize pathogen reduction. If the controller 38 is programmed to prioritize optimization of pathogen reduction over optimization of bacterial testing (e.g., due to the preferences of the center), it may be advantageous for the controller 38 to assess pathogen reduction optimization before assessing bacterial testing optimization (and possibly automatically distribute the fluid so as to optimize pathogen reduction, if practicable). However, it is within the scope of the present disclosure for the controller 38 to assess the practicability of differing approaches to fluid distribution in any order without departing from the scope of the present disclosure.

Figure 4A:
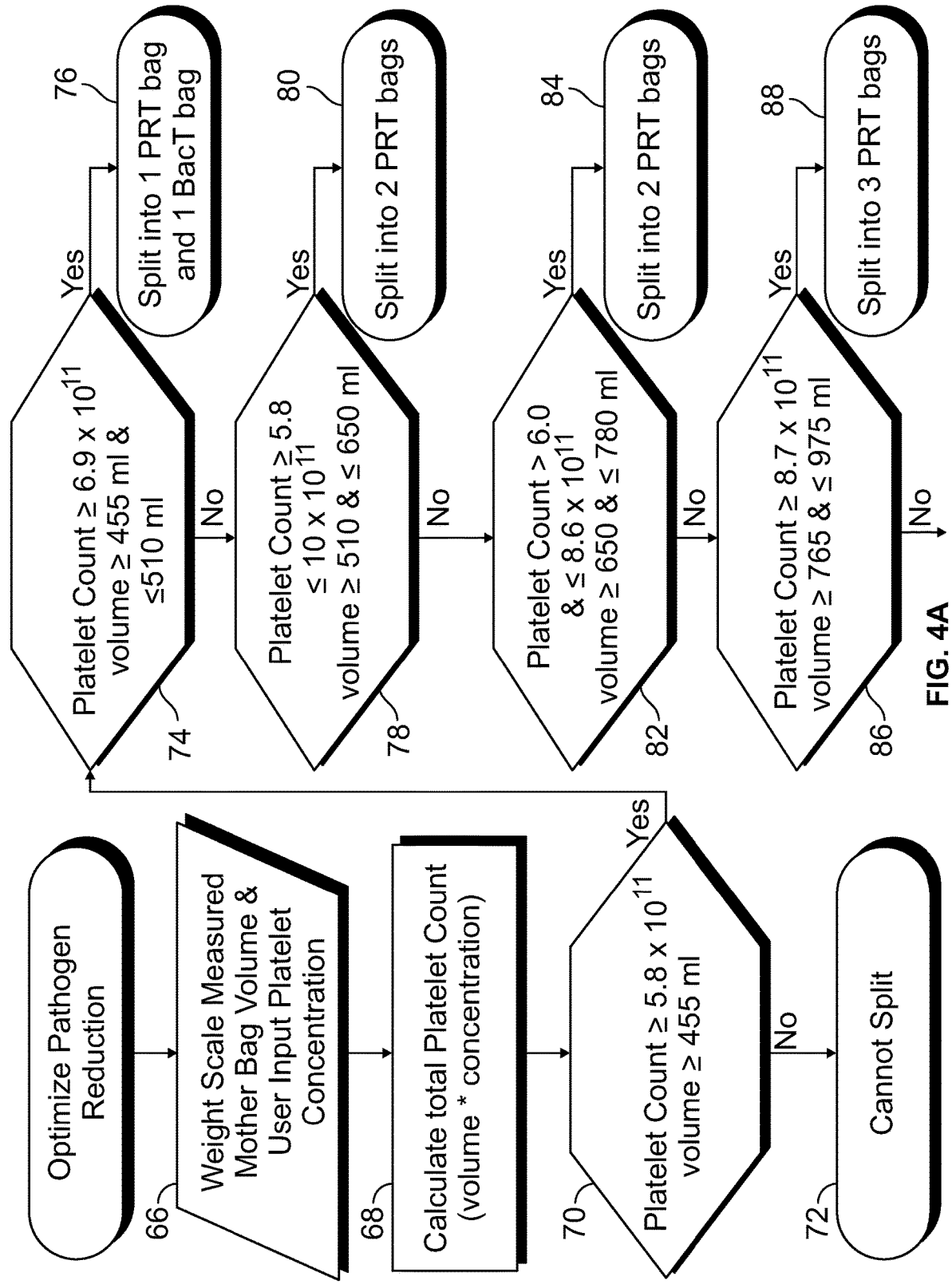
FIGS. 4A and 4B are two portions of a flowchart of another exemplary approach to splitting a fluid into uneven volumes, according to an aspect of the present disclosure.
Figure 4B:
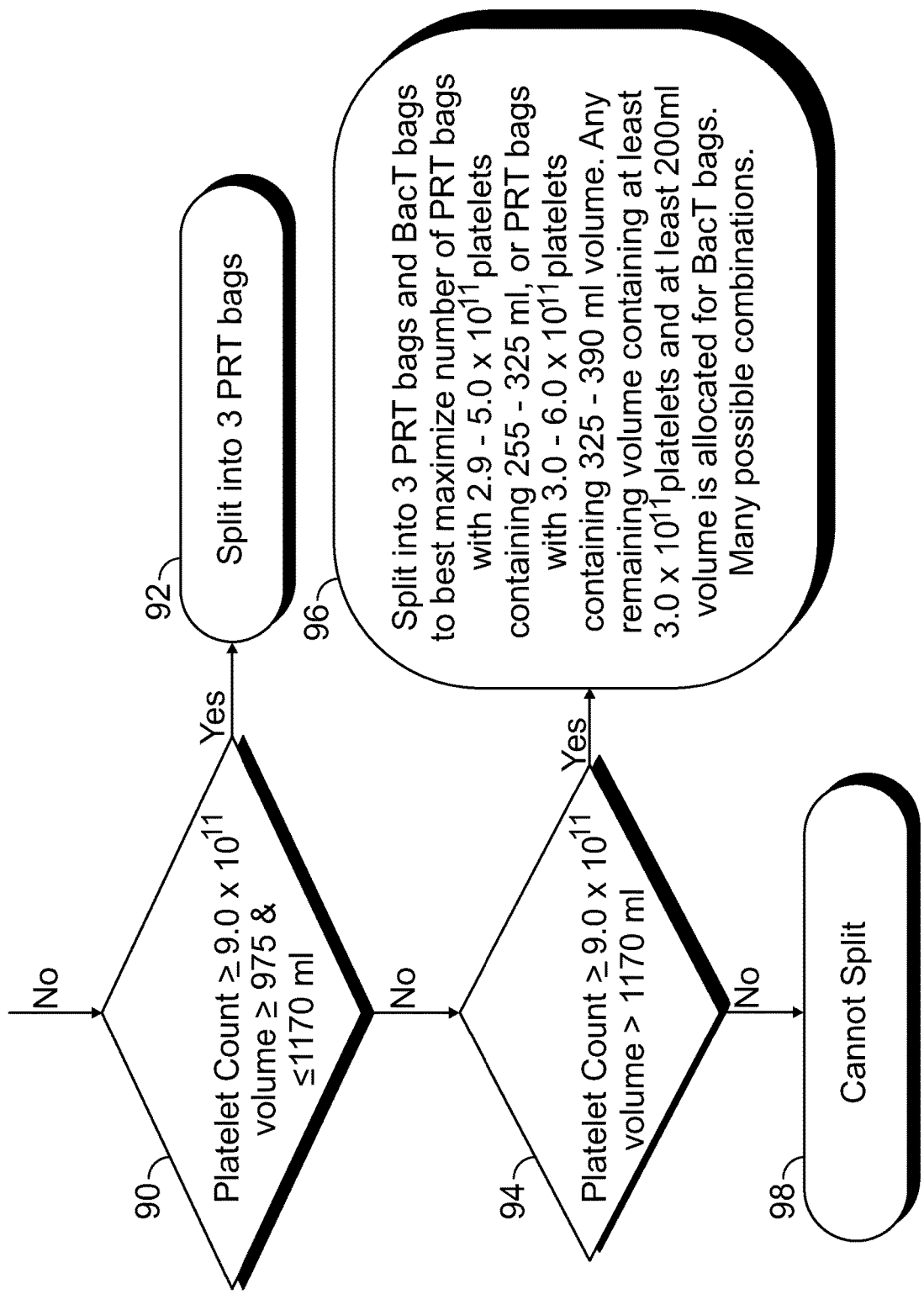

In any event, FIGS. 4A and 4B show an exemplary algorithm that may be executed by the controller 38 in order to determine a distribution for optimizing pathogen reduction. In a first step (indicated at 50 in FIG. 4A), the weight scales 26 determine the total weight of the fluid flow circuit 18 (which may be used to determine the volume of the fluid to be split), with the controller 38 receiving the platelet concentration of the fluid as an input. The controller 38 then determines the relevant characteristics of the fluid. In the embodiment of FIG. 4A, the relevant characteristics of the fluid are the platelet count and the volume of the fluid (as when assessing optimization of bacterial testing), but the relevant characteristics of the fluid may be different without departing from the scope of the present disclosure. In the illustrated embodiment, the controller 38 uses the platelet concentration and the volume of the fluid to determine the amount of platelets in the fluid (by multiplying the volume of the fluid by the platelet concentration), as shown in FIG. 4A as step 68. As described above, rather than receiving a constituent concentration as an input, the controller 38 may instead receive a platelet count as an input during step 66, in which case step 68 may be omitted (or instead modified to calculate platelet concentration, if necessary).

Once the relevant characteristics of the fluid have been determined, the controller 38 then determines whether the fluid is suitable for being split so as to optimize pathogen reduction. This determination may be made in any of a number of ways, with FIG. 4A showing a step 70 in which the controller 38 compares the platelet count and the volume of the fluid (which are the relevant characteristics in the illustrated embodiment) to minimum values to determine whether it is possible to split the high volume platelet product so as to optimize pathogen reduction. In the illustrated embodiment, the minimum platelet count for splitting is $5.8\times10^{11}$, while the minimum fluid volume is 455 ml, such that the controller 38 will determine (at step 72 of FIG. 4A) that pathogen reduction optimization is not a viable option or distribution. It should be understood that these minimum values are merely exemplary and that other minimum values may be employed without departing from the scope of the present disclosure. For example, different minimum values may be appropriate if the possible target volumes into which a high volume platelet product may be split are different from the ones described herein.

When the controller 38 determines that the high volume fluid is suitable to be distributed so as to optimize pathogen reduction, it considers the most appropriate distribution of the fluid based on the relevant characteristics of the fluid and the number of containers that are incorporated into the fluid flow circuit 18 mounted to the frame 12 (because the number of containers determines the maximum number of volumes into which the fluid may be split). In the illustrated embodiment, the fluid flow circuit 18 includes three containers 16, 22, and 24, such that the fluid may be split into either two or three volumes.

The controller 38 first determines whether the fluid is suitable to be split into one pathogen reduction volume and one bacterial testing volume. In the embodiment of FIG. 4A (in which a pathogen reduction volume has a volume of 255 ml and a bacterial testing volume has a volume of 200 ml), the controller 38 determines in step 74 whether the fluid contains at least $6.9\times10^{11}$ platelets and a volume between 455-510 ml. If so, the controller 38 determines (at step 76) that it is most optimal to split the fluid into one pathogen reduction volume and one bacterial testing volume. If the high volume platelet product has a volume of 455 ml, it will be distributed so as to create one pathogen reduction volume having a volume of 255 ml and one bacterial testing volume having a volume of 200 ml. This may include all of the fluid being conveyed from the source container 16 into the two satellite containers 22 and 24 or (perhaps more preferably) only an amount of fluid corresponding to one of the target volumes being transferred from the source container 16 to one of the satellite containers 22, 24 (with the remaining fluid being retained in the source container 16 as the other target volume). The latter approach may be preferred on account of it being completed more quickly than the former approach (as less fluid is conveyed out of the source container 16), but both approaches are within the scope of the present disclosure.

If the high volume platelet product has a volume greater than 455 ml (but less than 510 ml), one or both of the target volumes will include an additional amount of fluid. The controller 38 may either distribute all of the excess fluid between the two satellite containers 22 and 24 (if the fluid flow circuit 18 is provided with at least two satellite containers), distribute all of the excess fluid to a single satellite container (while retaining an exact target volume in the source container 16), or retain at least a portion of the excess fluid in the source container 16. The controller 38 may distribute the excess fluid in any distribution without departing from the scope of the present disclosure. For example, the controller 38 may be configured to convey only the minimum amount of fluid from the source container 16 to one of the satellite containers 22, 24, while retaining the remaining fluid in the source container 16. Thus, if the high volume platelet product has a volume of 500 ml, the controller 38 may execute a fluid-splitting procedure in which 200 ml of fluid are conveyed into one of the satellite containers 22, 24 (as a bacterial testing volume), with the remaining 300 ml remaining in the source container 16 (as a 255 ml pathogen reduction volume with 45 ml of excess fluid). In another embodiment, if a satellite container 22, 24 has a maximum capacity, the controller 38 may be configured to fill the satellite container 22, 24 to its capacity (or to a particular percentage of its capacity), with the remainder of the fluid being retained in the source container 16.

If the controller 38 determines in step 74 that pathogen reduction is not optimized by distributing the fluid into one pathogen reduction volume and one bacterial testing volume (e.g., due to there being more than 510 ml of fluid to distribute in the embodiment of FIG. 4A), the controller 38 determines whether the fluid is suitable to be split into two "small volume" pathogen reduction volumes. In the embodiment of FIG. 4A (in which a "small volume" pathogen reduction volume has a volume of 255-325 ml), the controller 38 determines in step 78 whether the fluid contains $5.8$-$10.0 \times 10^{11}$ platelets and a volume between 510 and 650 ml. If so, the controller 38 determines (at step 80) that it is most optimal to split the fluid into two "small volume" pathogen reduction volumes. Depending on the exact volume of the fluid, the two "small volume" pathogen reduction volumes may have the same or different volumes. For example, if the high volume platelet product has a volume of 510 ml, it will be distributed so as to create two "small volume" pathogen reduction volumes each having a volume of 255 ml. This may include all of the fluid being conveyed from the source container 16 into the two satellite containers 22 and 24 or (perhaps more preferably) only an amount of fluid corresponding to one of the target volumes being transferred from the source container 16 to one of the satellite containers 22, 24 (with the remaining fluid being retained in the source container 16 as the other target volume). As explained above, the latter approach may be preferred on account of it being completed more quickly than the former approach, due to less fluid being conveyed out of the source container 16, though both approaches are within the scope of the present disclosure.

On the other hand, if the high volume platelet product has a volume greater than 510 ml, the controller 38 may distribute the fluid into equal or unequal volumes. As when splitting the fluid into two equal "small volume" amounts, the controller 38 may either distribute the fluid between two satellite containers (if available) or may convey a selected amount into one satellite container 22, 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to one of the satellite containers 22, 24, while retaining the remaining fluid in the source container 16. Thus, if the high volume platelet product has a volume of 600 ml, the controller 38 may execute a fluid-splitting procedure in which 255 ml of fluid are conveyed into one of the satellite containers 22, 24, with the remaining 345 ml remaining in the source container 16. In another embodiment, if the satellite containers 22 and 24 have a maximum capacity, the controller 38 may be configured to fill one of the satellite containers 22, 24 to its capacity (or to a particular percentage of its capacity), with the remainder of the fluid being retained in the source container 16.

If the controller 38 determines in step 78 that pathogen reduction is not optimized by distributing the fluid into two "small volume" pathogen reduction volumes, the controller 38 determines whether the fluid is suitable to be split into two "large volume" pathogen reduction volumes. In the embodiment of FIG. 4A (in which a "large volume" pathogen reduction volume has a volume of 325-390 ml), the controller 38 determines in step 82 whether the fluid contains $6.0$-$8.6 \times 10^{11}$ platelets and a volume between 650 and 780 ml. If so, the controller 38 determines (at step 84) that it is most optimal to split the fluid into two "large volume" pathogen reduction volumes. Depending on the exact volume of the fluid, the two "large volume" pathogen reduction volumes may have the same or different volumes. For example, if the high volume platelet product has a volume of 650 ml, it will be distributed so as to create two "large volume" pathogen reduction volumes each having a volume of 325 ml. This may include all of the fluid being conveyed from the source container 16 into the two satellite containers 22 and 24 or (perhaps more preferably) only an amount of fluid corresponding to one of the target volumes being transferred from the source container 16 to one of the satellite containers 22, 24 (with the remaining fluid being retained in the source container 16 as the other target volume). As explained above, the latter approach may be preferred on account of it being completed more quickly than the former approach, due to less fluid being conveyed out of the source container 16, though both approaches are within the scope of the present disclosure.

On the other hand, if the high volume platelet product has a volume greater than 650 ml, the controller 38 may distribute the fluid into equal or unequal volumes. As when splitting the fluid into two equal "large volume" amounts, the controller 38 may either distribute the fluid between two satellite containers (if available) or may convey a selected amount into one satellite container 22, 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to one of the satellite containers 22, 24, while retaining the remaining fluid in the source container 16. Thus, if the high volume platelet product has a volume of 700 ml, the controller 38 may execute a fluid-splitting procedure in which 325 ml of fluid are conveyed into one of the satellite containers 22, 24, with the remaining 375 ml remaining in the source container 16. In another embodiment, if the satellite containers 22 and 24 have a maximum capacity, the controller 38 may be configured to fill one of the satellite containers 22, 24 to its capacity (or to a particular percentage of its capacity), with the remainder of the fluid being retained in the source container 16.

If the controller 38 determines in step 82 that pathogen reduction is not optimized by distributing the fluid into two "large volume" pathogen reduction volumes, the controller 38 determines whether the fluid is suitable to be split into three "small volume" pathogen reduction volumes. In the embodiment of FIG. 4A (in which a "small volume" pathogen reduction volume has a volume of 255-325 ml), the controller 38 determines in step 86 whether the fluid contains at least $8.7 \times 10^{11}$ platelets and a volume between 765 and 975 ml. If so, the controller 38 determines (at step 88) that it is most optimal to split the fluid into three "small volume" pathogen reduction volumes. Depending on the exact volume of the fluid, the three "small volume" pathogen reduction volumes may have the same or different volumes. For example, if the high volume platelet product has a volume of 765 ml, it will be distributed so as to create three "small volume" pathogen reduction volumes each having a volume of 255 ml. If the fluid flow circuit 18 includes only two satellite containers 22 and 24, portions of the fluid are transferred to the satellite containers 22 and 24, while the remainder is retained in the source container 16. However, if the fluid flow circuit includes at least three satellite containers, all of the fluid may instead be transferred from the source container to the satellite containers. As explained above, it may be preferred for a target volume to remain in the source container 16 due to such a fluid-splitting procedure being completed more quickly (on account of less fluid being conveyed out of the source container 16), though both approaches are within the scope of the present disclosure.

On the other hand, if the high volume platelet product has a volume greater than 765 ml, the controller 38 may distribute the fluid into equal or unequal volumes. As when splitting the fluid into three equal amounts, the controller 38 may either distribute the fluid between three satellite containers (if available) or may convey a selected amount into two satellite containers 22 and 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to the two satellite containers 22 and 24, while retaining the remaining fluid in the source container 16. Thus, if the high volume platelet product has a volume of 800 ml, the controller 38 may execute a fluid-splitting procedure in which 255 ml of fluid are conveyed into each of the satellite containers 22 and 24, with the remaining 290 ml remaining in the source container 16. In another embodiment, if the satellite containers 22 and 24 have a maximum capacity, the controller 38 may be configured to fill the satellite containers 22 and 24 to their capacity (or to a particular percentage of their capacity), with the remainder of the fluid being retained in the source container 16.

If the controller 38 determines in step 86 that pathogen reduction is not optimized by distributing the fluid into three "small volume" pathogen reduction volumes, the controller 38 determines whether the fluid is suitable to be split into three "large volume" pathogen reduction volumes. In the embodiment of FIG. 4B (in which a "large volume" pathogen reduction volume has a volume of 325-390 ml), the controller 38 determines in step 90 whether the fluid contains at least $9.0 \times 10^{11}$ platelets and a volume between 975 and 1,170 ml. If so, the controller 38 determines (at step 92) that it is most optimal to split the fluid into three "large volume" pathogen reduction volumes. Depending on the exact volume of the fluid, the three "large volume" pathogen reduction volumes may have the same or different volumes. For example, if the high volume platelet product has a volume of 975 ml, it will be distributed so as to create three "large volume" pathogen reduction volumes each having a volume of 325 ml. If the fluid flow circuit 18 includes only two satellite containers 22 and 24, portions of the fluid are transferred to the satellite containers 22 and 24, while the remainder is retained in the source container 16. However, if the fluid flow circuit includes at least three satellite containers, all of the fluid may instead be transferred from the source container to the satellite containers. As explained above, it may be preferred for a target volume to remain in the source container 16 due to such a fluid-splitting procedure being completed more quickly (on account of less fluid being conveyed out of the source container 16), though both approaches are within the scope of the present disclosure.

On the other hand, if the high volume platelet product has a volume greater than 975 ml, the controller 38 may distribute the fluid into equal or unequal volumes. As when splitting the fluid into three equal amounts, the controller 38 may either distribute the fluid between three satellite containers (if available) or may convey a selected amount into two satellite containers 22 and 24, while retaining an appropriate amount of fluid in the source container 16. If the controller 38 determines to distribute the fluid into unequal volumes, it may employ any distribution without departing from the scope of the present disclosure. For example, the controller 38 may be configured to convey only the minimum amount of fluid from the source container 16 to the two satellite containers 22 and 24, while retaining the remaining fluid in the source container 16. Thus, if the high volume platelet product has a volume of 1000 ml, the controller 38 may execute a fluid-splitting procedure in which 325 ml of fluid are conveyed into each of the satellite containers 22 and 24, with the remaining 350 ml remaining in the source container 16. In another embodiment, if the satellite containers 22 and 24 have a maximum capacity, the controller 38 may be configured to fill the satellite containers 22 and 24 to their capacity (or to a particular percentage of their capacity), with the remainder of the fluid being retained in the source container 16.

Finally, if the controller 38 determines in step 90 that pathogen reduction is not optimized by distributing the fluid into three "large volume" pathogen reduction volumes, the controller 38 determines whether the fluid is suitable to be split into some other distribution that optimizes pathogen reduction. In the embodiment of FIG. 4B, the controller 38 determines in step 94 whether the fluid contains at least $9.0 \times 10^{11}$ platelets and a volume greater than 1,170 ml. If so, the controller 38 determines (at step 96) that some other distribution is possible to optimize pathogen reduction. As indicated in FIG. 4B, depending on the exact volume and platelet count of the fluid, any of a number of possible distributions may be optimal. In general, the controller 38 considers the fluid characteristics (platelet count and volume, in the illustrated embodiment) of the different target volumes that are available (e.g., bacterial testing volume, "small volume" pathogen reduction volume, "large volume" pathogen reduction volume, and "dual storage" pathogen reduction volume) and the number of containers incorporated into the fluid flow circuit 18, and determines how to best distribute the fluid based on those parameters. This may include splitting the fluid into equal or unequal volumes and may include the controller 38 being programmed with a preference for one target volume over the others or with a particular hierarchy of the available target volumes (e.g., based upon the objectives and preferences of the center) or with any other logic for determining how to distribute the fluid.

If the controller 38 determines in step 94 that the fluid does not have characteristics falling within the specified ranges (e.g., due to the platelet count being too low for the volume), the controller 38 determines that the fluid cannot be distributed so as to optimize pathogen reduction (at step 98). On the other hand, if the controller 38 has determined that pathogen reduction may be optimized (by splitting the fluid into one of the distributions presented in the embodiment of FIGS. 4A and 4B), it may present an operator (e.g., in region 48 of the operator interface station 40) with optimization of pathogen reduction as a possible distribution or, alternatively, proceed to automatically distribute the fluid so as to optimize pathogen reduction (if the controller 38 has been programmed with optimization of pathogen reduction as a top priority or preference).

While a number of possible target volumes are presented above, it should be understood that these target volumes are merely exemplary and that other target volumes may be employed without departing from the scope of the present disclosure. This may include requiring an additional amount of fluid (as a safety factor) to be included in each target volume. For example, it may be advantageous to require a bacterial testing volume to have a volume of at least 205 ml (i.e., 5 ml of extra fluid) to better ensure that enough fluid is provided to proceed with bacterial testing. In one embodiment, the controller 38 is configured to allow an operator to select or specify the magnitude of the extra amount of fluid or the safety factor to be incorporated into each target volume, with the safety factor being the same for all of the different target volumes or different for at least two of the target volumes (e.g., with a "dual storage" pathogen reduction volume having a larger safety factor, on account of the fluid being split into two units after pathogen reduction).

The system 10 is shown and described above as a standalone device, but it should be understood that it may be incorporated into a larger assembly or otherwise paired with another fluid processing device. For example, in one embodiment, if the fluid to be split is a biological fluid, such as a blood component (which may be, without limitation, a high volume platelet product), the system may be paired with an apheresis system, such as the AMICUS® system manufactured by Fenwal, Inc. of Lake Zurich, Illinois, which is an affiliate of Fresenius Kabi AG of Bad Homburg, Germany. In such an implementation, blood is separated by the apheresis system into two or more components, with a high volume platelet product (or other fluid) being produced by the apheresis system. The high volume platelet product or other fluid is conveyed from the apheresis system directly into a source container 16 being supported by the source support 14. With the high volume platelet product or other fluid in the source container 16, a fluid-splitting procedure of the type described above may be executed. If practicable, this may be more time-efficient than separating the blood using an apheresis system, transporting a fluid produced by the apheresis system to the fluid-splitting system (which may be located at a different site than the apheresis system), and then splitting the fluid using the fluid-splitting system.

Incorporating the system 10 into a larger assembly or otherwise pairing it with another fluid processing device may include fluidly connecting a fluid flow circuit configured to be mounted to the system with a fluid flow circuit configured to be mounted to a separate fluid processing device. This may be achieved according to any suitable approach (e.g., using a luer connector), but in one embodiment, may be achieved by sterile connection of conduits of the two fluid flow circuits according to the approaches described in U.S. Pat. Nos. 9,199,070 or 10,040,247, both of which are hereby incorporated herein by reference.

Aspects

Aspect 1. A system for splitting a fluid, comprising: a source support configured to support a source container of a fluid flow circuit; a satellite support configured to support a satellite container of the fluid flow circuit fluidly connected to the source container; a weight scale associated with each of the supports; a clamp assembly; and a controller configured to receive an input corresponding to a concentration or an amount of a constituent in a fluid to be split, control each weight scale to measure a combined weight of the container and the contents of the container supported by the support associated with the weight scale, determine a plurality of possible distributions of the fluid to be split between the source container and the satellite container based at least in part on the concentration or amount of said constituent and the combined weight measured by each weight scale, and control the clamp system to selectively allow and prevent fluid flow from the source container to the satellite container so as to distribute the fluid to be split between the source container and the satellite container according to one of said plurality of possible distributions, wherein at least one of said plurality of possible distributions is an uneven distribution of the fluid to be split.

Aspect 2. The system of Aspect 1, wherein said constituent comprises platelets, and a first of said plurality of possible distributions is based upon optimization of bacterial testing of the fluid to be split and a second of said plurality of possible distributions is based upon optimization of pathogen reduction of the fluid to be split.

Aspect 3. The system of Aspect 2, wherein the controller is configured to determine that optimization of bacterial testing of the fluid to be split is not a possible distribution when the amount of platelets in the fluid to be split is less than $6.0 \times 10^{11}$ and/or when a volume of the fluid to be split is less than 400 ml.

Aspect 4. The system of any one of Aspects 2-3, wherein the controller is configured to determine that optimization of pathogen reduction is not a possible distribution when the amount of platelets in the fluid to be split is less than $5.8 \times 10^{11}$ and/or when a volume of the fluid to be split is less than 455 ml.

Aspect 5. The system of Aspect 2, wherein one of said plurality of possible distributions would create at least two pathogen reduction volumes having different volumes.

Aspect 6. The system of any one of the preceding Aspects, wherein the controller is further configured to allow an operator to select between at least two of said plurality of possible distributions prior to the controller controlling the clamp system to selectively allow and prevent fluid flow from the source container to the satellite container so as to distribute the fluid to be split between the source container and the satellite container according to the distribution selected by the operator.

Aspect 7. The system of Aspect 6, wherein the controller is further configured to allow the operator to select a distribution that is different from said at least two of said plurality of possible distributions.

Aspect 8. The system of any one of Aspects 1-5, wherein the controller is further configured to automatically distribute the fluid to be split according to one of said plurality of possible distributions without an operator selecting which of said plurality of possible distributions is to be employed.

Aspect 9. The system of any one of the preceding Aspects, wherein the controller is further configured to be programmed or provided with two or more different target volumes into which the fluid to be split may be distributed, and the controller is further configured to distribute the fluid to be split into said two or more different target volumes so as to minimize a remainder amount of the fluid.

Aspect 10. The system of any one of the preceding Aspects, wherein the controller is further configured to be programmed or provided with one or more target volumes into which the fluid to be split may be distributed, the controller is further configured to control the clamp system so as to include an extra amount of the fluid to be split in each target volume, and the controller is further configured to allow an operator to select a magnitude of said extra amount of fluid.

Aspect 11. A method of automatically splitting a fluid, comprising: receiving an input corresponding to a concentration or an amount of a constituent in a fluid in a source container to be split between the source container and a satellite container; measuring a combined weight for each container and the contents of the container; determining a plurality of possible distributions of the fluid to be split between the source container and the satellite container based at least in part on the concentration or amount of said constituent and the combined weights; and automatically controlling a clamp system to selectively allow and prevent fluid flow from the source container to the satellite container so as to distribute the fluid to be split between the source container and the satellite container according to one of said plurality of possible distributions, wherein at least one of said plurality of possible distributions is an uneven distribution of the fluid to be split.

Aspect 12. The method of Aspect 11, wherein said constituent comprises platelets, and a first of said plurality of possible distributions is based upon optimization of bacterial testing of the fluid to be split and a second of said plurality of possible distributions is based upon optimization of pathogen reduction of the fluid to be split.

Aspect 13. The method of Aspect 12, further comprising determining that optimization of bacterial testing of the fluid to be split is not a possible distribution when the amount of platelets in the fluid to be split is less than $6.0 \times 10^{11}$ and/or when a volume of the fluid to be split is less than 400 ml.

Aspect 14. The method of any one of Aspects 12-13, further comprising determining that optimization of pathogen reduction is not a possible distribution when the amount of platelets in the fluid to be split is less than $5.8 \times 10^{11}$ and/or when a volume of the fluid to be split is less than 455 ml.

Aspect 15. The method of Aspect 12, wherein one of said plurality of possible distributions would create at least two pathogen reduction volumes having different volumes.

Aspect 16. The method of any one of Aspects 11-15, further comprising allowing an operator to select between at least two of said plurality of possible distributions prior automatically controlling the clamp system to selectively allow and prevent fluid flow from the source container to the satellite container so as to distribute the fluid to be split between the source container and the satellite container according to the distribution selected by the operator.

Aspect 17. The method of Aspect 16, further comprising allowing the operator to select a distribution that is different from said at least two of said plurality of possible distributions.

Aspect 18. The method of any one of Aspects 11-15, further comprising automatically distributing the fluid to be split according to one of said plurality of possible distributions without an operator selecting which of said plurality of possible distributions is to be employed.

Aspect 19. The method of any one of Aspects 11-18, wherein the fluid is to be split into two or more different target volumes, and the method further comprises distributing the fluid to be split into said two or more different target volumes so as to minimize a remainder amount of the fluid.

Aspect 20. The method of any one of Aspects 11-19, wherein the fluid is to be split into one or more target volumes, the method further comprises automatically controlling the clamp system so as to include an extra amount of the fluid to be split in each target volume, and the method further comprises allowing an operator to select a magnitude of said extra amount of fluid.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A system for splitting a fluid, comprising:
a source support configured to support a source container of a fluid flow circuit;
a satellite support configured to support a satellite container of the fluid flow circuit fluidly connected to the source container;
a weight scale associated with each of the supports;
a clamp assembly; and
a controller configured to
 receive an input corresponding to a concentration or an amount of a constituent in a fluid to be split,
 control each weight scale to measure a combined weight of the container and the contents of the container supported by the support associated with the weight scale,
 determine a plurality of possible distributions of the fluid to be split between the source container and the satellite container based at least in part on the concentration or amount of said constituent and the combined weight measured by each weight scale, and
 control the clamp system to selectively allow and prevent fluid flow from the source container to the satellite container so as to distribute the fluid to be split between the source container and the satellite container according to one of said plurality of possible distributions, wherein at least one of said plurality of possible distributions is an uneven distribution of the fluid to be split.

2. The system of claim 1, wherein
said constituent comprises platelets, and
a first of said plurality of possible distributions is based upon optimization of bacterial testing of the fluid to be split and a second of said plurality of possible distributions is based upon optimization of pathogen reduction of the fluid to be split.

3. The system of claim 2, wherein the controller is configured to determine that optimization of bacterial testing of the fluid to be split is not a possible distribution when the amount of platelets in the fluid to be split is less than $6.0 \times 10^{11}$ and/or when a volume of the fluid to be split is less than 400 ml.

4. The system of claim 2, wherein the controller is configured to determine that optimization of pathogen reduction is not a possible distribution when the amount of platelets in the fluid to be split is less than $5.8 \times 10^{11}$ and/or when a volume of the fluid to be split is less than 455 ml.

5. The system of claim 2, wherein one of said plurality of possible distributions would create at least two pathogen reduction volumes having different volumes.

6. The system of claim 1, wherein the controller is further configured to allow an operator to select between at least two of said plurality of possible distributions prior to the controller controlling the clamp system to selectively allow and prevent fluid flow from the source container to the satellite container so as to distribute the fluid to be split between the source container and the satellite container according to the distribution selected by the operator.

7. The system of claim 6, wherein the controller is further configured to allow the operator to select a distribution that is different from said at least two of said plurality of possible distributions.

8. The system of claim 1, wherein the controller is further configured to automatically distribute the fluid to be split according to one of said plurality of possible distributions without an operator selecting which of said plurality of possible distributions is to be employed.

9. The system of claim 1, wherein
the controller is further configured to be programmed or provided with two or more different target volumes into which the fluid to be split may be distributed, and
the controller is further configured to distribute the fluid to be split into said two or more different target volumes so as to minimize a remainder amount of the fluid.

10. The system of claim 1, wherein
the controller is further configured to be programmed or provided with one or more target volumes into which the fluid to be split may be distributed,
the controller is further configured to control the clamp system so as to include an extra amount of the fluid to be split in each target volume, and
the controller is further configured to allow an operator to select a magnitude of said extra amount of fluid.

11. The system of claim 1, wherein the controller is configured to
receive the input corresponding to the concentration of said constituent in the fluid to be split, and
determine said plurality of possible distributions of the fluid to be split between the source container and the satellite container based at least in part on the concentration of said constituent and the combined weight measured by each weight scale.

12. The system of claim 1, wherein the controller is configured to
receive the input corresponding to the amount of said constituent in the fluid to be split, and
determine said plurality of possible distributions of the fluid to be split between the source container and the satellite container based at least in part on the amount of said constituent and the combined weight measured by each weight scale.

* * * * *